(12) United States Patent
Augustine et al.

(10) Patent No.: US 6,511,501 B1
(45) Date of Patent: Jan. 28, 2003

(54) INFLATABLE THERMAL PAD WITH DRAINAGE

(75) Inventors: Scott Douglas Augustine, Bloomington, MN (US); Thomas P. Anderson, Savage, MN (US)

(73) Assignee: Augustine Medical, Inc., Eden Prairie, MN (US)

( * ) Notice: Subject to any disclaimer, the term of this patent is extended or adjusted under 35 U.S.C. 154(b) by 0 days.

(21) Appl. No.: 09/561,642

(22) Filed: May 2, 2000

Related U.S. Application Data

(63) Continuation of application No. 09/120,083, filed on Jul. 21, 1998, now Pat. No. 6,102,936.

(51) Int. Cl.[7] .................................................. A61F 7/00
(52) U.S. Cl. ........................ 607/96; 607/107; 5/606; 5/423
(58) Field of Search ................................ 607/107, 104, 607/96; 5/606, 423

(56) References Cited

U.S. PATENT DOCUMENTS

| | | | | |
|---|---|---|---|---|
| 2,930,594 A | * | 3/1960 | MacCracken | ............... 607/104 |
| 3,089,153 A | * | 5/1963 | Bosc | |
| 3,778,851 A | | 12/1973 | Howorth | |
| 3,867,939 A | * | 2/1975 | Moore et al. | ............... 604/291 |
| 4,867,230 A | * | 9/1989 | Voss | ........................... 165/46 |
| 5,022,110 A | | 6/1991 | Stroh | |
| 5,165,400 A | * | 11/1992 | Berke | ........................ 607/104 |
| 5,184,612 A | * | 2/1993 | Augustine | ................... 128/400 |
| 5,265,599 A | * | 11/1993 | Stephenson et al. | ........ 607/104 |
| 5,300,102 A | | 4/1994 | Augustine et al. | ........... 607/107 |
| 5,562,875 A | * | 10/1996 | Miller et al. | ............ 264/177.16 |
| 5,603,690 A | * | 2/1997 | Barry | ......................... 601/148 |
| 5,640,727 A | * | 6/1997 | Kappel | .......................... 5/423 |
| 5,640,728 A | * | 6/1997 | Graebe | .......................... 5/423 |
| 5,655,237 A | * | 8/1997 | Suzuki et al. | ................... 5/423 |
| 5,683,441 A | * | 11/1997 | Dickerhoff et al. | ......... 607/107 |
| 5,702,375 A | * | 12/1997 | Angelillo et al. | ........... 604/358 |
| 5,735,890 A | * | 4/1998 | Kappel et al. | ................. 5/423 |
| 5,800,489 A | * | 9/1998 | Augustine | ................... 607/104 |
| 5,860,292 A | * | 1/1999 | Augustine et al. | .......... 607/107 |

FOREIGN PATENT DOCUMENTS

| | | |
|---|---|---|
| DE | 33 20771 | 12/1984 |
| EP | 0 757 907 | 2/1997 |
| GB | 1 350 110 | 4/1974 |
| GB | 2 228 193 | 8/1990 |

OTHER PUBLICATIONS

Search Report for PCT/US99/12622.

* cited by examiner

*Primary Examiner*—Linda C. M. Dvorak
*Assistant Examiner*—Jocelyn Ram
(74) *Attorney, Agent, or Firm*—Gray Cary Ware & Freidenrich; Terrance A. Meador

(57) ABSTRACT

An inflatable convective thermal pad is adapted for use under a patient. The pad has a surface on a layer that receives the patient and that provides for the passage of air through the layer and the surface toward the patient. One or more drain openings or channels are provided in the layer for draining fluid from the layer.

35 Claims, 4 Drawing Sheets

INFLATABLE THERMAL PAD WITH DRAINAGE

This application is a continuation of U.S. patent application Ser. No. 09/120,083, filed Jul. 21, 1998, U.S. Pat. No. 6,102,936.

BACKGROUND OF THE INVENTION

1. Field of the Invention

The invention relates to an inflatable thermal pad. With greater particularly, the invention relates to an inflatable thermal pad adaptable for use in a variety of settings. More particularly still, the invention relates to an inflatable thermal pad with a top layer for receiving a person to be warmed, the pad having provision for drainage of fluid from a surface of the top layer.

2. Background

Hypothermia affects many people. Many of those for whom hypothermia goes untreated suffer a variety of adverse effects. For example, patients under general anesthesia lose the ability to regulate their own body temperature ("thermoregulate") and therefore fail to maintain the normal body temperature ("normothermia") necessary for proper physiological functioning. The inability to thermoregulate leads to a drop in body core temperature that can result in serious complications with potential for a fatal outcome. Patients that have been warmed during surgery avoid these complications. Furthermore, these actively warmed patients benefit by experiencing decreased blood and fluid loss, fewer wound infections, and better metabolization of drugs. Recent years have seen significant advances in techniques and devices for treatment and prevention of hypothermia. The Bair Huggerg family of systems and products produced and sold by Augustine Medical, Inc., the assignee of this patent application, are a pioneering example. Such products have provided tremendous benefits for the world patient population. These products are based upon warming by means that are primarily convective. In this regard, a light, flexible inflatable device is inflated with warm air and placed over a patient. Means in a bottom surface of the device expel the warm air, which bathes the patient and creates a warmed environment about the patient, thereby reducing the transfer of heat from the patient to the environment. Such devices are referred to generally as inflatable thermal blankets. Examples of such devices abound. See, for example, U.S. Pat. No. 5,300,102 assigned to Augustine Medical, Inc. The '102 patent is incorporated herein in its entirety by this reference.

Prior to the introduction of inflatable thermal blankets, modalities for warming patients included circulating water mattresses, warmed cotton blankets, fluid infusion warming devices, and radiant heat lamps. All of these modalities have limitations and problems associated with their use. With the introduction of the inflatable thermal blanket by Augustine Medical, Inc., clinicians have been able to provide safe and effective thermal therapy to patients in a number of clinical settings, including surgery and recovery.

Healthcare institutions have realized significant benefits from the introduction of inflatable thermal blankets. When patients are actively warmed they require less recovery time in a post-operating recovery unit. This saves hospital time, labor, and money. Furthermore, patients that are warmed have a higher degree of comfort and are more likely to have positive experiences and attitudes during and after treatment. The result is a happy, cooperative patient.

While there are many benefits related to warming patients using convective means, there are also many benefits well known in the literature that are derived from cooling patients using convective means. Therefore, it should be understood that this discussion and the invention to be described may pertain to both warming and cooling.

The opportunity to aid patient well being and improve patient thermal comfort is not limited to operating rooms and recovery units. Presently, in the healthcare setting, patients undergo a variety of procedures in a variety of clinical situations that invite patient thermoregulation. Inflatable thermal blankets are used to service these various other treatment settings, including intensive care units, neonatal care units, cardiac catheterization laboratories, chemotherapy labs, and other diagnostic rooms where magnetic resonance imaging (MRI) or computed axial tomography (CAT) scans take place.

Trauma rooms often receive patients that have lost large amounts of fluid and/or blood. Such patients may be unconscious. In these cases, immediate stabilization is required to prevent an irreversible downward cascade of physiological function. These patients are often hypothermic and the degree of hypothermia has been shown to correlate with death rates. Furthermore, these patients require immediate visual and tactile access. Patients undergoing diagnostic procedures generally already suffer from increased anxiety and/or illness related to their conditions. Diagnostic facilities utilizing MRI and CAT procedures are often cold and sterile environments because of the requirements for proper equipment function. These areas have the challenge of keeping patients comfortable and quiet during what could be prolonged sessions. Chemotherapy and catheterization laboratories also serve patients that are able to move around, are conscious, and are aware of their comfort level. In all of these settings, patients are exposed to cool and ambient environments and may also be exposed to fluids that exacerbate the cooling effect of the ambient environments.

In neonatal intensive care units (NICU), clinicians require frequent and unimpeded access to very small patients. Having such access while maintaining a warm environment poses a significant challenge that has not been met to a satisfactory degree by currently available inflatable thermal blankets. One limitation of the current convective warming technology as embodied in inflatable thermal blankets is the need to attach a thermal blanket to a neonatal patient in order to provide thermal care space. Patients undergoing procedures in the NICU may be conscious and may necessarily undergo frequent repositioning. Attaching a thermal blanket over a patient in this situation is not practical. Typically, such a device is attached to a patient by tape. Newborns have highly sensitive skin. Manifestly, the repeated placement and removal of adhesive tape to the skin of newborn patients is not desirable.

As clinicians have become aware of the benefits of treating and preventing hypothermia with convective means, the limitations of currently available inflatable thermal blankets with respect to specific patients, specific procedures, and specific environments have become evident.

SUMMARY OF THE INVENTION

Our invention is an inflatable convective thermal pad adaptable for use in a variety of clinical settings. This inflatable thermal pad can be placed under a patient to accommodate the need for access to the patient. The versatile and unique design of the inflatable thermal pad also accommodates the characteristics of specific treatment sites and treatment modalities.

Preferably, our pad is placed underneath the patient to facilitate access to the patient and to accommodate various patient positions. The pad has at least two layers of material, joined at a periphery to create an inflatable article. At least one layer, preferably the top layer, is adapted to provide for the passage of air through itself so that, when the pad is inflated with an input of pressurized, warmed air, the warmed air passes from the inflatable article through the top layer. A patient disposed on the top layer is warmed by the air passing through the layer. Preferably, the at least two layers also are joined within the periphery at at least one location. At least one inflation port opening into the pad is provided for the input of pressurized, warmed air that inflates the pad. One or more drain openings or channels are provided in the top layer for draining fluid from the top layer.

One or more extensions of the pad project beyond the periphery and provide enough area to either partially cover a patient or to stabilize the pad with respect to a support surface.

Our invention solves many problems associated with warming or cooling by means of the inflatable thermal blankets of the prior art. Consider for example, a patient in a catheterization lab. The patient, while sedated, is fully conscious and able to move around. In the cardiac catheterization procedure, a clinician examines heart function by inserting a flexible catheter into the heart through a blood vessel in an extremity of the patient. A radiographic dye is injected into the catheter to provide contrast for X-rays. During this procedure, externalized fluids can cause discomfort and undesirable evaporative cooling. Our invention provides a device that is well adapted for this procedure and well suited for solving this problem. In this regard, the pad is placed on a patient support surface, with the patient being received on the upper layer when the pad is inflated with warmed air. The warm air passes through the top layer and warms the patient. The one or more drain openings on the top layer facilitate removal of externalized fluids that might otherwise accumulate between the patient and the top layer.

Accordingly, an objective of our invention is to provide an inflatable thermal pad having a layer that supports a person while assisting in regulation of the person's core temperature by passing air through the layer of the pad on which the person is supported. A particular advantage of the invention is the ability of the pad to drain fluid from the layer during the pad's operation. Another advantage is the provision of an extension of the pad that may serve to either to lie over the patient in order to trap air between the patient and the pad, or to attach to a patient supporting structure in order to stabilize the pad on the structure.

DETAILED DESCRIPTION OF THE PREFERRED EMBODIMENTS

This description concerns an inflatable thermal pad that may be constructed using techniques and materials with which inflatable thermal blankets of the prior art are fabricated. These methods and materials generally contemplate bringing together and bonding two or more sheets of flexible material at a periphery, and at multiple points within the periphery to form an inflatable structure. This may be accomplished, for example, in a continuous web manufacturing process by multiple webs of materials. However, this is not intended to limit our invention exclusively to such methods. Indeed, we contemplate many possible manufacturing modes using many materials.

Figure 1:
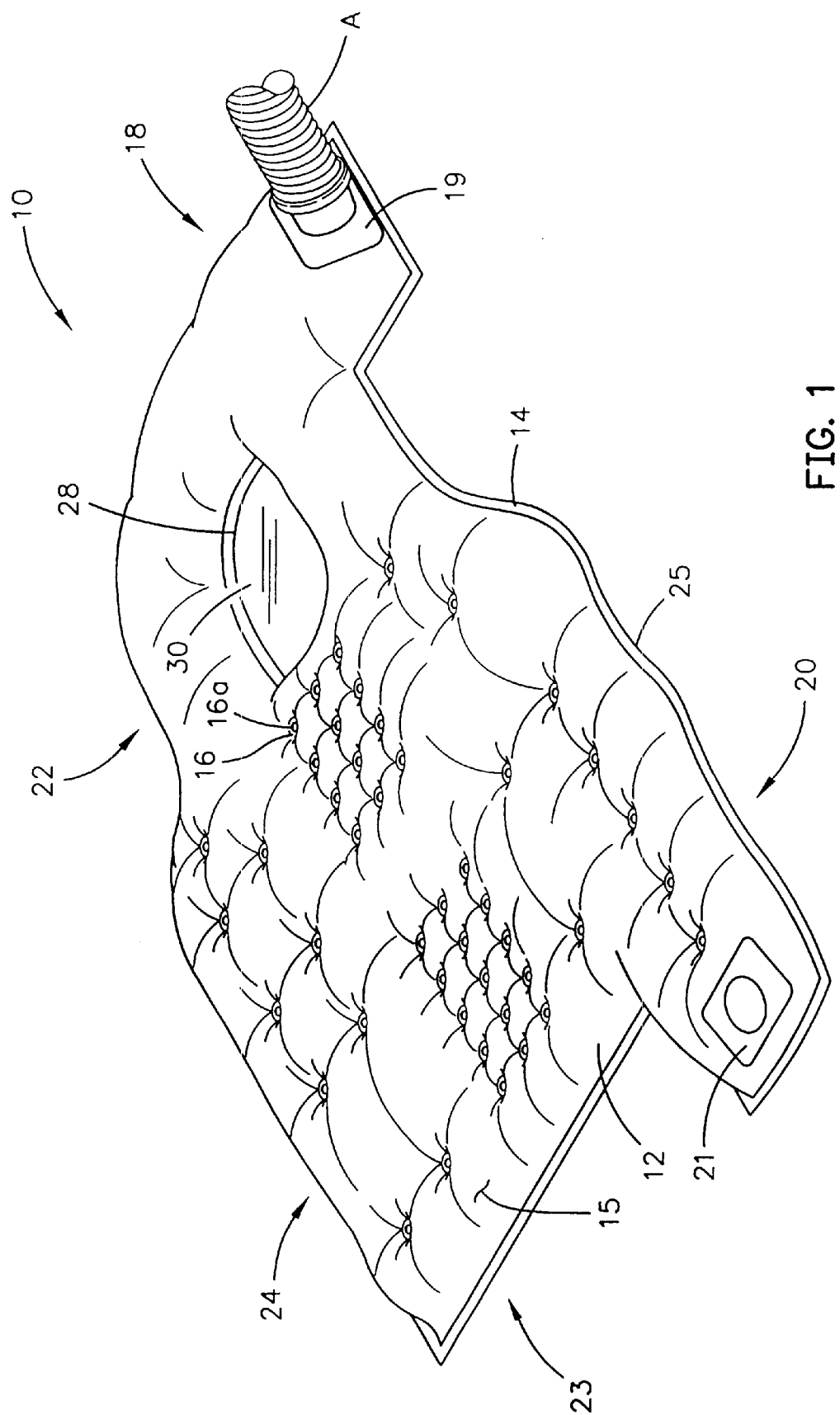
FIG. 1 is a perspective view of our inflatable thermal pad, when inflated.

Referring to FIG. 1, an inflatable thermal pad 10 according to our invention includes at least two layers of material that are brought together at a periphery. One of the layers 12 is denominated as the "top layer" in this description. The top layer 12 is the layer that receives a person and is also the layer through which a pressurized, warmed air passes to assist in regulating the core temperature of the person received on the layer 12. The periphery of the inflatable thermal pad 10 is indicated by the reference numeral 14. The top layer 12 is brought together with a bottom layer (that is not shown in FIG. 1) at at least one location within the periphery 14. In FIG. 1 the at least one location is indicated by reference numeral 16; in fact, the top layer 12 may be brought together with the bottom layer at a plurality of locations such as the location 16. In order to provide an input of pressurized and thermally regulated air to inflate the pad 10, at least one inflation port 18 is provided in the pad 10. A relatively stiff collar 19 of material is provided for receiving the end of an air hose A. Another end (not shown) of the air hose A may be connected to a source of pressurized, warmed air, such as the heater/blower that is illustrated in the incorporated patent. The air is conducted through the air hose A through the inflation inlet 18 whence it flows throughout the interior of the pad 10 between the top and bottom layers of the pad 10 and causes the pad 10 to inflate. More than one inflation port may be provided. For example, the port 20 with inflation collar 21 is shown in FIG. 1. The unused inflation port or ports would, of course, be sealed in order to prevent the exit of the pressurized gas during operation of the pad 10.

The inflatable thermal pad of our invention may have a characteristic shape. For example, in the pad 10 of FIG. 1, the periphery 14 defines a generally bell-shaped article having a head portion 22 with a first width, an end portion 23 with a second width greater than the first width, and two sides 24 and 25. A continuous closed seam 28 in the head portion 22 between the top and bottom layers of the pad 10 defines an area 30 that may be uninflatable, or inflatable to a lesser degree than the rest of the pad 10. The area 30 is of a shape and size to receive the back of the head of a person received on the top layer 12.

When inflated, the upper surface 15 of the top layer 12 of the pad 10 exhibits a sharply-varying topography with many wells and crevices. The wells are formed at the locations where the top layer 12 is brought together with the bottom layer. For example, at the location 16, there is a definite well formed when the pad 10 is inflated. Fluid externalized during treatment of a person supported on the pad 10 can collect in these wells. Collected fluid can inhibit the operation of the pad 10. If brought into contact with the skin of a person being warmed by the pad 10, fluid collected in these wells can cause conductive and evaporative cooling of the person.

Figure 2A:
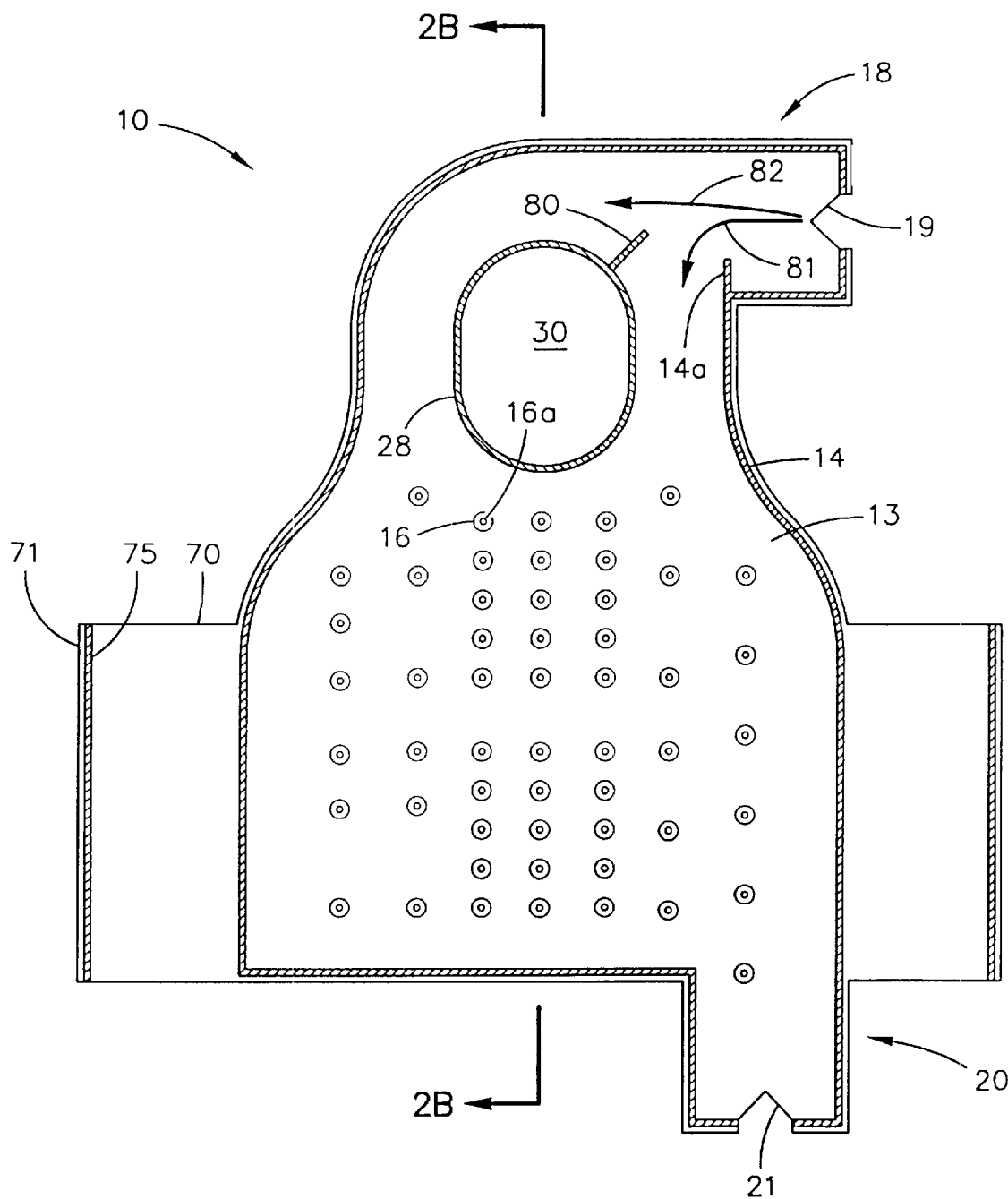
FIG. 2A is a partially schematic top plan view of the pad of FIG. 1.
Figure 2B:
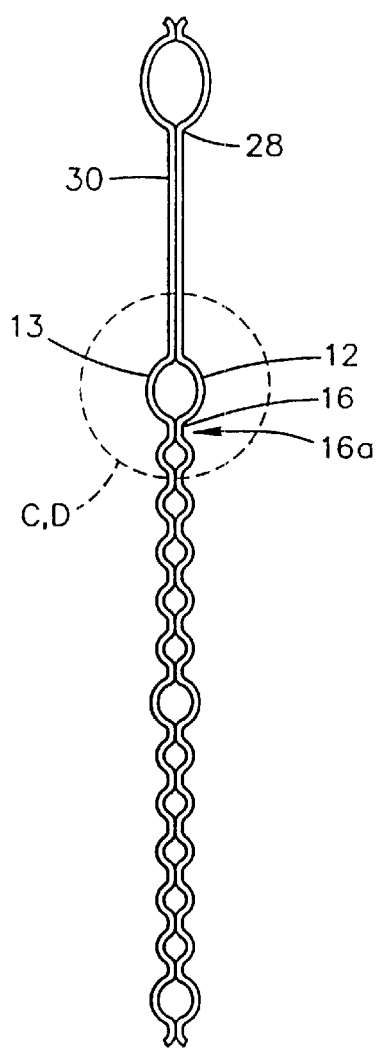
FIG. 2B is a side sectional view along B—B of FIG. 2A.
Figure 2C:
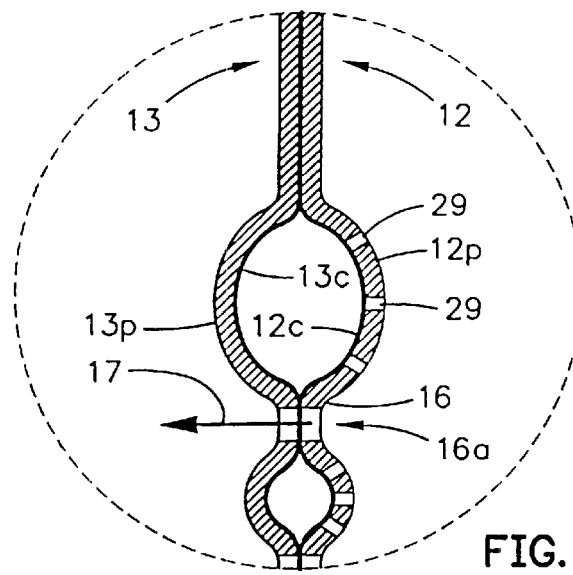
FIG. 2C and FIG. 2D are magnified views of a portion of the pad enclosed in the circle CD of FIG. 2B.
Figure 2D:
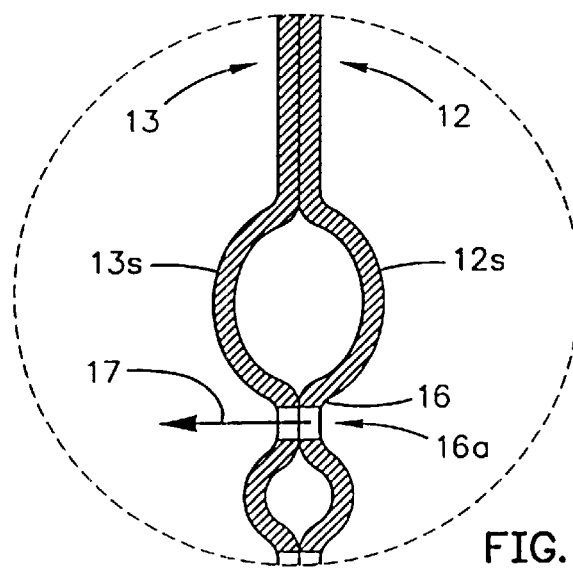

FIGS. 2A, 2B, 2C and 2D illustrate an element of our invention that drains fluid away from the top layer 12 of our inflatable thermal pad 10. In this regard, FIG. 2A illustrates a partially schematic top plan view of our inflatable thermal pad 10 in which the top layer 12 is invisible, thereby revealing the trace of the periphery 14, the closed seam 28, and the one or more locations 16. FIG. 2B shows a side sectional view of our inflatable thermal pad taken along B—B in FIG. 2A, with both the top and bottom layers being visible. Circle C, D in FIG. 2B encloses a portion of the pad 10 that is magnified in FIGS. 2C and 2D to show how drainage is provided according to one embodiment of our pad. These figures show the top layer 12 brought together with a bottom layer 13 at the periphery 14, along the closed seam 28, and at the one or more locations 16. With respect to the location indicated by the reference 16, FIGS. 2B, 2C, and 2D show a drain passage or channel 16a that opens through the top and bottom layers 12 and 13 to drain fluid from the top layer 12 through the pad 10 in the direction of the arrow 17. As seen in FIG. 2A, the location 16 where the top and bottom layers 12 and 13 are brought together has a first area that in plan, is larger than and encloses the area of the drain passage 16a. As will be described in more detail, the top layer 12 and bottom layer 13 are joined at the location 16 by an air-impermeable structure such as a bond or seal. At the one or more locations, the layers 12 and 13 are either brought together or are structurally continuous. The drain passage 16a occupies a position within the location 16 that maintains the integrity of the air-impermeable structure between the top layer and bottom layer so as to prevent pressurized air from exiting the pad 10 at the one or more locations 16.

FIG. 2C shows a possible pad construction in which both the top layer 12 and bottom layer 13 are made from a polyester non-woven extrusion 12p and 13p, each with a coating of polypropylene 12c and 13c on one side. The top layer 12 may have holes 29 formed by punching, slitting, or cutting to permit the flow of pressurized air from the pad through the top layer 12. Note that holes 29 can be opened through both layers 12 and 13 to make the pad 10 reversible. When the pad is assembled, the polypropylene-coated side 12c of the top layer 12 is sealed to the polypropylene-coated side 13c of the bottom layer 13 at the periphery 14, the seam 28, and the one or more locations 16 to form the pad. Ultrasonic welding may be used for this purpose as may RF sealing or heat sealing. Alternatively, the top layer 12 and bottom layer may each include a laminate of polypropylene and polyolefin web with holes formed in at least the top layer 12 to support passage of pressurized air. FIG. 2D shows another possible pad construction that uses spunbond-meltblown-spunbond (SMS) laminate sheets 12s and 13s. SMS materials are air permeable, yet have excellent fluid barrier properties. The use of these materials would preclude having to form passages to support the flow of pressurized air through the top layer 12. However, where sealed together at the periphery and one or more locations, SMS sheets would be air impermeable. Many other materials are contemplated, including washable textile fabrics or wovens that may be sewn in the proper configuration.

Figure 3:
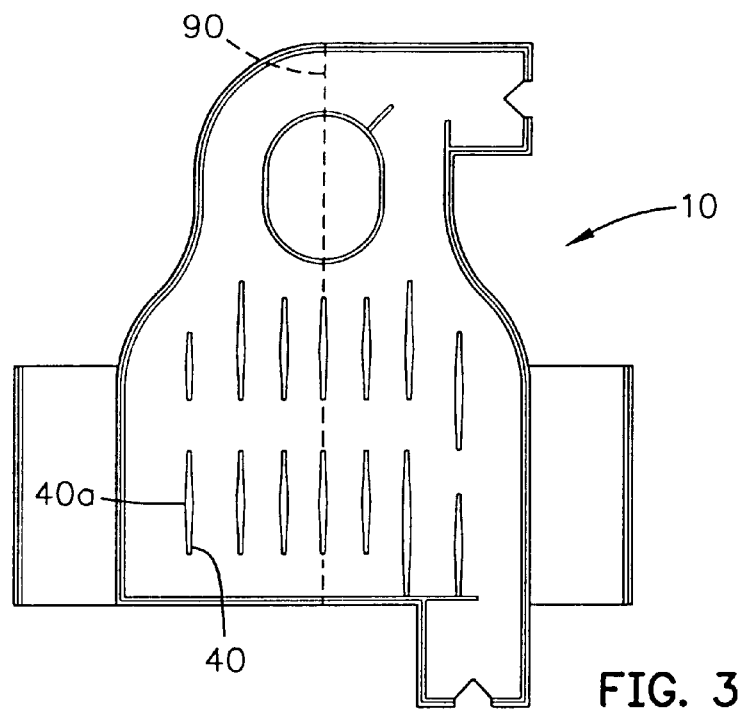
FIG. 3 is a partially schematic top plan view of a first alternate embodiment of the inflatable thermal pad.
Figure 4:
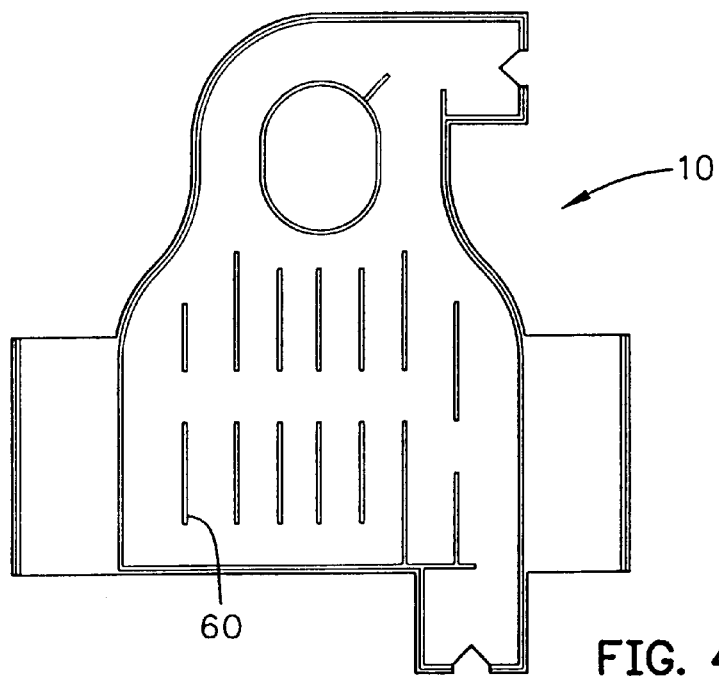
FIG. 4 is a partially schematic top plan view of the second alternate embodiment of the inflatable thermal pad.

As shown in FIGS. 1, 2A, 2B, 2C and 2D, the top and bottom layers 12 and 13 ad brought together continuously at the periphery 14 and the seam 28, and are brought together at substantially circular stake points in the locations 16. However, the shape of the location 16 within the periphery 14 is not intended to be limited to a circular, round, or oval shape. Any appropriate shape may be used, so long as it occupies enough area to support a drain passage and does not compromise the inflatability of the pad 10. In this regard, FIG. 3 shows but one alternate configuration for such a location in the form of an elongate seal 40 having an elongate drain passage 40a that opens through top and bottom layers of the pad 10. We further contemplate that the drain passages may be formed not only during construction of the pad 10, but also after its construction, when deployed. In this regard, FIG. 4 shows a location 60 where the top and bottom layers are joined in the shape of an elongate seam. We contemplate that the seam at location 60 may contain a line of weakness or a sequence perforations that could be opened by insertion of an instrument or by pulling to create a drain passage.

Other features of our inflatable thermal pad 10 may be understood with reference to FIG. 2A. In this regard, one or more flexible non-inflatable (or partially-inflatable) sections 70 ("flaps" or "drapes") formed integrally with the pad 30 may be provided along the periphery 14. For example, in FIG. 2A, two flaps 70 are shown, one on each side of the end portion 23. With respect to the flap 70, it includes an outer edge 71 along either or both sides of which one or more traces of adhesive 75 (or double-sided adhesive tape with a release liner) may be placed. The flap 70, and any others like it that maybe provided on the pad 10, has one of two functions. First, it can be disposed upwardly over the upper surface 15 of the top layer 12, positioned over the body of a person supported on that surface in order to assist in the trapping of air and the retention of warmth about the person's body. The second function includes folding the one or more flaps downwardly, beneath the bottom surface 13 so that the pad 10 can be anchored by the trace of adhesive 75 to an apparatus or structure on which the pad 10 is supported. The one or more flaps may be formed by an extension of the bottom layer 13, the top layer 12, or both layers, in which case the layers would be brought together to act as a single integral piece.

Another feature of the pad 10 is indicated by an elongate location 80 that extends from the seam 28 in a direction that is generally transverse to the direction in which pressurized air flows into the inflatable pad 10 when the air hose A is connected at the collar 19. As the pad inflates, the location 80 acts as a baffle that deflects a portion of the incoming stream of pressurized air in the direction 81, while the remainder of the pressurized air flows in the direction 82. This deflection tends to equalize the pressure of air flowing into an inflating the pad 10, when the air is introduced through the inflation port 18 at the head end of the pad 10.

FIG. 3 has yet another feature of the pad illustrated by the perforation or line of weakness 90. The inflatable pad 10 may also include the line of weakness 90 to enable users to separate portions of the pad to in order to facilitate removal from or placement around the patient. For example, a perforation may be included on the center line of the pad that runs from the foot end to substantially near the head end of the pad to facilitate parting of the pad at the mid-line. This will enable clinicians to remove the pad from underneath the patient Without having to lift a patient off the pad. This may be particularly important in the cases where patients are to remain immobilized due to injuries of the head and neck and movement may be detrimental to the patient. This line of weakness could just as effectively be located on the side to side axis or a transverse axis of the pad.

The invention of this patent application concerns an inflatable thermal pad having a surface for receiving a person and provision for expelling air through the surface toward the person while providing for drainage of fluids from the surface. Although the invention has been described with reference to a number of embodiments and further with reference to a specific shape for an inflatable thermal pad, it is submitted that, broadly, the invention would be embodied in any inflatable thermal pad having a provision for draining fluid from a surface of the pad that has the dual function of receiving a person and convecting air from within the pad toward the person in response to inflation of the pad. The invention is not limited to the bell-shaped pad that is shown nor is it limited to such a pad with either circular or longitudinal drainage openings.

Clearly, the other embodiments and modifications of this invention will occur readily to those of ordinary skill in the art in view of these teachings. Therefore, this invention is to be limited only by following claims, which include all such embodiments and modifications when viewed in conjunction with the above specification and accompanying drawings.

We claim:

1. An inflatable thermal pad, including:
   an inflatable structure with a periphery, a bottom layer and a top layer, the top layer configured to vent air from within the inflatable structure through the top layer;
   at least one inflation port opening for delivering air into the inflatable structure;
   a baffle between the bottom layer and the top layer, the baffle being positioned to direct at least a portion of the air delivered into the inflatable structure from the at least one inflation port toward a particular region of the inflatable structure; and
   the pad is configured to drain fluid from at least a portion of the top layer.

2. The pad of claim 1, wherein at least one opening extends through the top layer for draining the fluid from the top layer.

3. The pad of claim 1, wherein at least one opening extends through the top layer and the bottom layer for draining the fluid from the top layer.

4. The pad of claim 1, wherein the top layer is air permeable and the bottom layer is air permeable.

5. The pad of claim 1, wherein the periphery defines sides of the pad and further including a sheet of flexible material on at least one of the sides.

6. The pad of claim 1, further comprising:
   a line of weakness for parting of the pad along the line of weakness.

7. The pad of claim 1, wherein the top layer is formed from materials selected from a group consisting of a polyester extrusion with a polypropylene coating, a laminate of polypropylene and polyolefin web and a spunbound-meltblown-spunbound laminate.

8. The pad of claim 1, wherein each of the top layer and the bottom layers are formed from materials selected from a group consisting of a polyester extrusion with a polypropylene coating, a laminate of polypropylene and polyolefin web and a spunbound-meltblown-spunbound laminate.

9. The pad of claim 1, wherein the baffle is positioned adjacent to the at least one inflation port opening.

10. The pad of claim 1, wherein the periphery defines at least a head section and an end section, further including a head receiving portion in the head section and wherein the baffle directs the air to a first side of the head receiving portion.

11. The pad of claim 1, wherein the baffle extends outward from the head receiving portion.

12. The pad of claim 11, wherein the baffle directs a first portion of the air to a first side of the head receiving portion and a second portion of the air toward a second side of the head receiving portion.

13. An inflatable thermal pad, including:
    an inflatable structure with a periphery, a bottom layer and a top layer, the top layer configured to vent air from within the inflatable structure through the top layer and the bottom layer configured to vent air from within the inflatable structure through the bottom layer;
    at least one inflation port opening for delivering air into the inflatable structure; and
    a baffle between the bottom layer and the top layer, the baffle being positioned to direct at least a portion of the air delivered into the inflatable structure from the at least one inflation port toward a particular region of the inflatable structure.

14. The pad of claim 13, wherein the baffle is positioned adjacent to the at least one inflation port opening.

15. The pad of claim 13, wherein the periphery defines at least a head section and an end section, further including a head receiving portion in the head section and wherein the baffle directs the air to a first side of the head receiving portion.

16. The pad of claim 15, wherein the baffle directs a first portion of the air to a first side of the head receiving portion and a second portion of the air toward a second side of the head receiving portion.

17. The pad of claim 13, wherein the pad is configured to drain fluid from at least a portion of the top layer.

18. The pad of claim 17, wherein at least one opening extends through the top layer for draining the fluid from the top layer.

19. The pad of claim 17, wherein at least one opening extends through the top layer and the bottom layer for draining the fluid from the top layer.

20. The pad of claim 13, wherein the top layer is air permeable and the bottom layer is air permeable.

21. The pad of claim 13, wherein the periphery defines sides of the pad and further including a sheet of flexible material on at least one of the sides.

22. The pad of claim 13, further comprising:
    a line of weakness for parting of the pad along the line of weakness.

23. The pad of claim 13, wherein the top layer is formed from materials selected from a group consisting of a polyester extrusion with a polypropylene coating, a laminate of polypropylene and polyolefin web and a spunbound-meltblown-spunbound laminate.

24. The pad of claim 13, wherein each of the top layer and the bottom layers are formed from materials selected from a group consisting of a polyester extrusion with a polypropylene coating, a laminate of polypropylene and polyolefin web and a spunbound-meltblown-spunbound laminate.

25. An inflatable thermal pad, including:
    an inflatable structure with a periphery, a bottom layer and a top layer, the top layer configured to vent air from within the inflatable structure through the top layer and being formed from materials selected from a group consisting of a polyester extrusion with a polypropylene coating, a laminate of polypropylene and polyolefin web and a spunbound-meltblown-spunbound laminate;
    at least one inflation port opening for delivering air into the inflatable structure; and
    the top layer is air permeable and the bottom layer is air permeable.

26. The pad of claim 25, wherein the periphery defines sides of the pad and further including a sheet of flexible material on at least one of the sides.

27. The pad of claim 25, further comprising:
    a line of weakness for parting of the pad along the line of weakness.

28. The pad of claim 25, wherein the bottom layer is formed from materials selected from a group consisting of a polyester extrusion with a polypropylene coating, a laminate of polypropylene and polyolefin web and a spunbound-meltblown-spunbound laminate.

29. The pad of claim 25, further comprising:

a baffle between the bottom layer and the top layer, the baffle being positioned to direct at least a portion of the air delivered into the inflatable structure from the at least one inflation port toward a particular region of the inflatable structure.

30. The pad of claim 25, wherein the baffle is positioned adjacent to the at least one inflation port opening.

31. The pad of claim 25, wherein the periphery defines at least a head section and an end section, further including a head receiving portion in the head section and wherein the baffle directs the air to a first side of the head receiving portion.

32. The pad of claim 31, wherein the baffle directs a first portion of the air to a first side of the head receiving portion and a second portion of the air toward a second side of the head receiving portion.

33. The pad of claim 25, wherein the pad is configured to drain fluid from at least a portion of the top layer.

34. The pad of claim 33, wherein at least one opening extends through the top layer for draining the fluid from the top layer.

35. The pad of claim 33, wherein at least one opening extends through the top layer and the bottom layer for draining the fluid from the top layer.

* * * * *